United States Patent [19]

Lake et al.

[11] 4,400,572

[45] Aug. 23, 1983

[54] HYDROCARBON CONVERSION

[75] Inventors: Ivan J. S. Lake, Middlesbrough; Thomas V. Whittam, Darlington, both of England

[73] Assignee: Imperial Chemical Industries PLC, London, England

[21] Appl. No.: 326,027

[22] Filed: Nov. 30, 1981

[30] Foreign Application Priority Data

Dec. 11, 1980 [GB] United Kingdom ............... 8039686

[51] Int. Cl.³ .............................................. C07C 5/22
[52] U.S. Cl. ................................................. 585/481
[58] Field of Search ........................................ 585/481

[56] References Cited

U.S. PATENT DOCUMENTS 4,245,130 1/1981 Jones et al. ...................... 585/481

*Primary Examiner*—Curtis R. Davis
*Attorney, Agent, or Firm*—Cushman, Darby & Cushman

[57] ABSTRACT

The process comprises isomerization, in the liquid or vapour phase, of a feed comprising a xylene or mixture of xylenes and optionally also containing up to 25% ethylbenzene using a catalyst comprising a novel crystalline aluminosilicate zeolite Nu-6(2).

10 Claims, No Drawings

HYDROCARBON CONVERSION

This invention relates to a process for the isomerisation of alkyl benzene hydrocarbons using a catalyst comprising new zeolite materials. The new zeolite materials will be referred to hereinafter as "zeolite Nu 6(1)" and "zeolite Nu 6(2)" or simply as "Nu6(1)" and "Nu6(2)".

Zeolites Nu6(1) and Nu6(2) and their preparation are described in our co-pending U.S. application Ser. No. 326,026, filed Nov. 30, 1981.

Zeolites Nu6(1) and Nu6(2) have a chemical composition, in terms of mole ratios of oxides, expressed by the formula 0.5 to 1.5 $R_2O:Y_2O_3$:at least 10 $XO_2$:0 to 2000 $H_2O$
wherein R is a monovalent cation or 1/n of a cation of valency n, X is silicon and/or germanium, Y is one or more of aluminum, iron, chromium, vanadium, molybdenum, antimony, arsenic, manganese, gallium, or boron, and $H_2O$ is water of hydration additional to water notionally present when R is H. Zeolite Nu-6(1) and Nu6(2) as prepared have X-ray patterns substantially as set out in Tables 1 and 2 (as determined by standard technique using copper $K\alpha$ radiation).

TABLE 1

| Zeolite Nu-6 (1) | |
|---|---|
| dA | 100I/Io |
| 13.4 | 89 |
| 11.3 | 6 |
| 6.89 | 3 |
| 5.46 | 13 |
| 4.52 | 17 |
| 4.48 | 15 |
| 4.29 | 84 |
| 4.23 | 19 |
| 3.998 | 100 |
| 3.683 | 34 |
| 3.478 | 40 |
| 3.382 | 91 |
| 3.335 | 61 |
| 3.107 | 13 |
| 3.019 | 11 |
| 2.986 | 3 |
| 2.964 | 3 |
| 2.484 | 17 |

Within the above definition of chemical composition, the number of moles of $XO_2$ is typically in the range 10 to 5000 and zeolites Nu-6(1) and Nu-6(2) appear to be most readily formed in a state of high purity when the number of moles of $XO_2$ is in the range 20 to 1000.

This definition includes both freshly prepared Nu-6(1) and Nu-6(2) ("freshly prepared" means the product of synthesis and washing, with optional drying, as hereinafter described) and also forms of it resulting from dehydration, and/or calcination, and/or ion exchange. In freshly prepared Nu6(1) and Nu6(2), R may include an alkali metal cation especially sodium, and/or ammonium, and hydrogen and usually or when prepared from nitrogen compounds, including nitrogen-containing organic cations as described below or cationic degradation products thereof, or precursors thereof. These nitrogen containing cations are hereinafter referred to as Q.

The freshly prepared Nu-6(1) and Nu-6(2) may also contain nitrogen-containing compounds well in excess of the 1.5 moles set out in the aforesaid definition of the composition of Nu-6(1) and Nu-6(2) typically in the range 0.1 to 20 moles per mole of $Y_2O_3$. Since Nu-6(1) and Nu-6(2) are zeolites, the nitrogen containing base must be physically trapped within the crystal lattice. It can be removed by thermal or oxidative degradation or by displacement by suitable small molecules. This physically trapped basic material does not constitute part of the composition for the purposes of the definition. Thus Nu-6(1) and Nu-6(2) as made typically have the following molar composition:

0 to 1.8 $M_2O$:1.0 to 400 $Q:Y_2O_3$:10 to 5000 $XO_2$:0 to 2000 $H_2O$ wherein M is an alkali metal and/or ammonium, and $M_2O + Q \geq 1.0$.

The $H_2O$ content of freshly prepared zeolite Nu-6(1) depends on the conditions in which it has been dried after synthesis. Indeed, if dried at temperatures at or above 200° C. it converts to zeolite Nu-6(2).

In calcined forms of zeolite Nu6(2), R may be alkali metal but includes less or no nitrogen-containing organic compounds, since these are burnt out in the presence of air, leaving hydrogen as the other balancing cation, or otherwise displaced prior to calcination.

A very surprising characteristic of zeolite Nu-6(1) which makes it unique in high silica zeolites, is its behaviour on heating. Thus when as made Nu-6(1) is heated at temperatures of from 200° to 750° C., it recrystallises to a noval crystalline phase designated zeolite Nu-6(2). Typical X-ray diffraction data for zeolite Nu-6(2) is given in Table 2.

TABLE 2

| Zeolite Nu-6 (2) | | | |
|---|---|---|---|
| dA | 100I/Io | dA | 100I/Io |
| 8.41 | 45 B | 3.94 | 2 B |
| 6.67 | 42 | 3.76 | 11 B |
| 6.09 | 15 B | 3.65 | 15 B |
| 4.61 | 27.5 | 3.44 | 27 B |
| 4.33 | 100 | 3.33 | 76 |
| ca 4.19 | Shoulder | 3.17 | 15 B |
| ca 4.10 | | 3.05 | 9 |

All diffraction lines show some broadening, those marked B are the broadest. Significant line broadening appears to be a characteristic of zeolite Nu-6(2). The degree of broadening depends upon the temperature as further discussed in our co-pending U.S. application Ser. No. 326,026, filed Nov. 30, 1981.

According to the present invention a hydrocarbons conversion process comprises contacting a feed of an alkylbenzene or a mixture of alkylbenzenes under isomerisation conditions in the vapour or liquid phase with a catalyst comprising zeolite Nu6-(2).

The catalyst used in the process of this invention may be zeolite Nu6-(2) per se but in a preferred embodiment of the process zeolite Nu6-(2) is used in the form of a physical mixture with a suitable diluent and/or binder, for example alumina, silica or a clay. Alumina is particularly preferred as a diluent, the amount of alumina present in the catalyst being preferably in the range 5 to 95% by weight based on total catalyst weight. The catalyst is conveniently used in the form of pellets, extrudates or other aggregates well known to those skilled in this art.

In the vapour phase, suitable isomerisation conditions for the process of this invention include a temperature in the range 100° to 600° C., preferably 200° to 450° C. and a pressure in the range 0.5 to 50, preferably 1 to 5, Kg/cm² absolute.

In the liquid phase embodiment of the process of this invention, suitable isomerisation conditions include a temperature in the range 0° to 350° C., a pressure in the range of 1 to 200, preferably 5 to 70, Kg/cm² absolute and, in a flow system, a space velocity in the range 0.1 to 100, preferably 0.5 to 30, w/w hour, the higher flow rates being used at the higher temperatures. Optionally a diluent is present, suitably one or more of those having a critical temperature higher than the isomerisation temperature being used and including toluene, trimethylbenzene, naphthenes and paraffins. Preferably, the diluent if present, amounts to 1 to 90% of the feed to the isomerisation reaction. In the above mentioned forms of the process of this invention the catalyst preferably contains no hydrogenation/dehydrogenation component.

Optionally the isomerisation reaction is conducted in the presence of hydrogen. A suitable mole ratio of hydrogen to alkylbenzene feed lies in the range 1:1 to 30:1. If hydrogen is used, it is preferred that the catalyst should comprise a metal of Group VIII of the Periodic Table together with the zeolite. Preferably the metal of Group VIII is platinum or nickel. The amount of metal used preferably lies in the range 0.1 to 2% by weight of metal based on the total weight of catalyst. If desired, the catalyst may contain one or more additional metals, for example rhenium, suitably in the range 0.1 to 2% by weight based on the total weight of catalyst.

Preferably the alkylbenzene is a xylene, for example m-xylene for conversion to p-xylene, or a mixture of xylenes, possibly with ethylbenzene. The amount of ethylbenzene present will depend to some extent on the source of the xylene mixture but will usually lie in the range 0 to 25% by weight of the feedstock. However, we believe that the process of this invention is very suitable for at least partial destruction of the ethylbenzene in feedstocks containing relatively large amounts of ethylbenzene, say in the range 6 to 25% by weight of the feedstock.

The invention is illustrated by the following Examples.

EXAMPLE 1

A sample of zeolite Nu-6(2) prepared as described in Example 3 of our co-pending U.S. application Ser. No. 326,026, filed Nov. 30, 1981 was formed into aggregates having diameters in the size range of 425 to 1000 μm. The zeolite's empirical formula was 0.25 Na$_2$O:Al$_2$O$_3$:77.4 SiO$_2$ and it contained 0.20% by weight sodium, 0.95% by weight aluminum and 36.8% by weight silicon.

The sample was charged to a glass reactor and heated in a stream of air at 500° C. for 16 hours. It was then cooled in a nitrogen stream to 400° C. A feedstock consisting mainly of C$_8$ aromatic hydrocarbons was passed over the aggregated zeolite for 18 hours at a weight hourly space velocity of 13.8. Details of the composition of the feed and of the product obtained after 8 hours and 18 hours are given in Table 3. All percentages given are by weight.

TABLE 3

| Hours on line | Feedstock | 8 hours | 18 hours |
|---|---|---|---|
| Benzene (%) | 0.02 | 1.64 | 1.34 |
| Toluene (%) | 1.75 | 2.22 | 2.12 |
| Ethylbenzene (%) | 8.61 | 6.16 | 6.74 |
| Paraxylene (%) | 7.94 | 18.92 | 18.49 |
| Metaxylene (%) | 50.92 | 44.06 | 44.08 |
| Orthoxylene (%) | 25.54 | 20.90 | 21.32 |
| C$_9$ + aromatics (%) | 3.86 | 4.88 | 4.49 |

TABLE 3-continued

| Hours on line | Feedstock | 8 hours | 18 hours |
|---|---|---|---|
| Paraxylene approach to equilibrium (%) | | 95.7 | 93.55 |
| Ethylbenzene loss (%) | | 28.4 | 21.72 |
| Xylene loss (%) | | 0.62 | 0.60 |

EXAMPLE 2

The sample of aggregated zeolite Nu-6(2) used in Example 1 was regenerated by heating in a stream of air at 500° C. for 16 hours. It was then cooled in a nitrogen stream to 400° C. A feedstock consisting mainly of C$_8$ aromatic hydrocarbons was passed over the aggregated zeolite for 6 hours at a weight hourly space velocity of 6.3. Details of the composition of the feed and of the product contained after 6 hours are given in Table 4. All percentages are given by weight.

TABLE 4

| | Feedstock | Product |
|---|---|---|
| Benzene (%) | 0.04 | 0.46 |
| Toluene (%) | 1.11 | 1.89 |
| Ethylbenzene (%) | 1.46 | 0.95 |
| Paraxylene (%) | 9.59 | 22.13 |
| Metaxylene (%) | 59.54 | 50.19 |
| Orthoxylene (%) | 27.46 | 22.84 |
| C$_9$ + aromatics (%) | 0.64 | 1.43 |
| Paraxylene approach to equilibrium (%) | | 98.71 |
| Ethylbenzene loss (%) | | 34.93 |
| Xylene loss (%) | | 1.48 |

From these results it can be seen that zeolite Nu-6(2) brings about the isomerisation of xylenes to close to equilibrium with very little loss of xylenes. Simultaneous loss of ethylbenzene is high.

We claim:

1. A hydrocarbon conversion process which comprises contacting a feed of an alkylbenzene or a mixture of alkylbenzenes under isomerisation conditions in the vapour or liquid phase with a catalyst comprising zeolite Nu6-(2).

2. A process as claimed in claim 1 in which zeolite Nu-6(2) is used in the form of a physical mixture with a diluent and/or binder.

3. A process as claimed in claim 1 in which the process is carried out in the vapour phase under isomerisation conditions which include a temperature in the range 100° to 600° C. and a pressure in the range 0.5 to 50 Kg/cm² absolute.

4. A process as claimed in claim 1 in which the process is carried out in the liquid phase under isomerisation conditions which include a temperature in the range 0° to 350° C. and a pressure in the range 1 to 200 Kg/cm².

5. A process as claimed in claim 1 in which the isomerisation reaction is carried out in the presence of hydrogen.

6. A process as claimed in claim 5 in which the mole ratio of hydrogen to alkylbenzene feed is in the range 1:1 to 30:1.

7. A process as claimed in claim 5 in which the catalyst comprises a metal of Group VIII of the Periodic Table together with zeolite Nu-6(2).

8. A process as claimed in claim 7 in which the amount of metal of Group VIII is in the range 0.1 to 2.0% by weight.

9. A process as claimed in claim 1 in which the alkylbenzene is a xylene or a mixture of xylene isomers.

10. A process as claimed in claim 1 in which the alkylbenzene feed contains up to 25% by weight of ethylbenzene.

* * * * *